United States Patent [19]

Bulteel

[11] 4,168,629
[45] Sep. 25, 1979

[54] APPARATUS FOR ULTRASONIC EXAMINATION

[75] Inventor: John B. Bulteel, Avon, England

[73] Assignee: Rolls-Royce Limited, London, England

[21] Appl. No.: 877,711

[22] Filed: Feb. 14, 1978

[30] Foreign Application Priority Data

Feb. 19, 1977 [GB] United Kingdom ............... 7089/77

[51] Int. Cl.² .......................................... G01N 29/04
[52] U.S. Cl. ...................................... 73/615; 73/620
[58] Field of Search ....................... 73/610, 614–616, 73/618, 620, 622, 627, 629

[56] References Cited

U.S. PATENT DOCUMENTS

| 3,856,985 | 12/1974 | Yokoi et al. | 73/629 X |
| 3,857,052 | 12/1974 | Beller | 73/620 X |

Primary Examiner—Anthony V. Ciarlante
Attorney, Agent, or Firm—Stevens, Davis, Miller & Mosher

[57] ABSTRACT

In apparatus for ultrasonic examination of an object, the echoes derived at successive positions of an ultrasonic transducer are digitized and subtracted one from the other. If the echoes are not the same, the difference is a discrete indication of a flaw. The invention applies especially to the detection of flaws close to the front surface of the object where the front surface echo tends to obscure nearby flaws.

5 Claims, 4 Drawing Figures

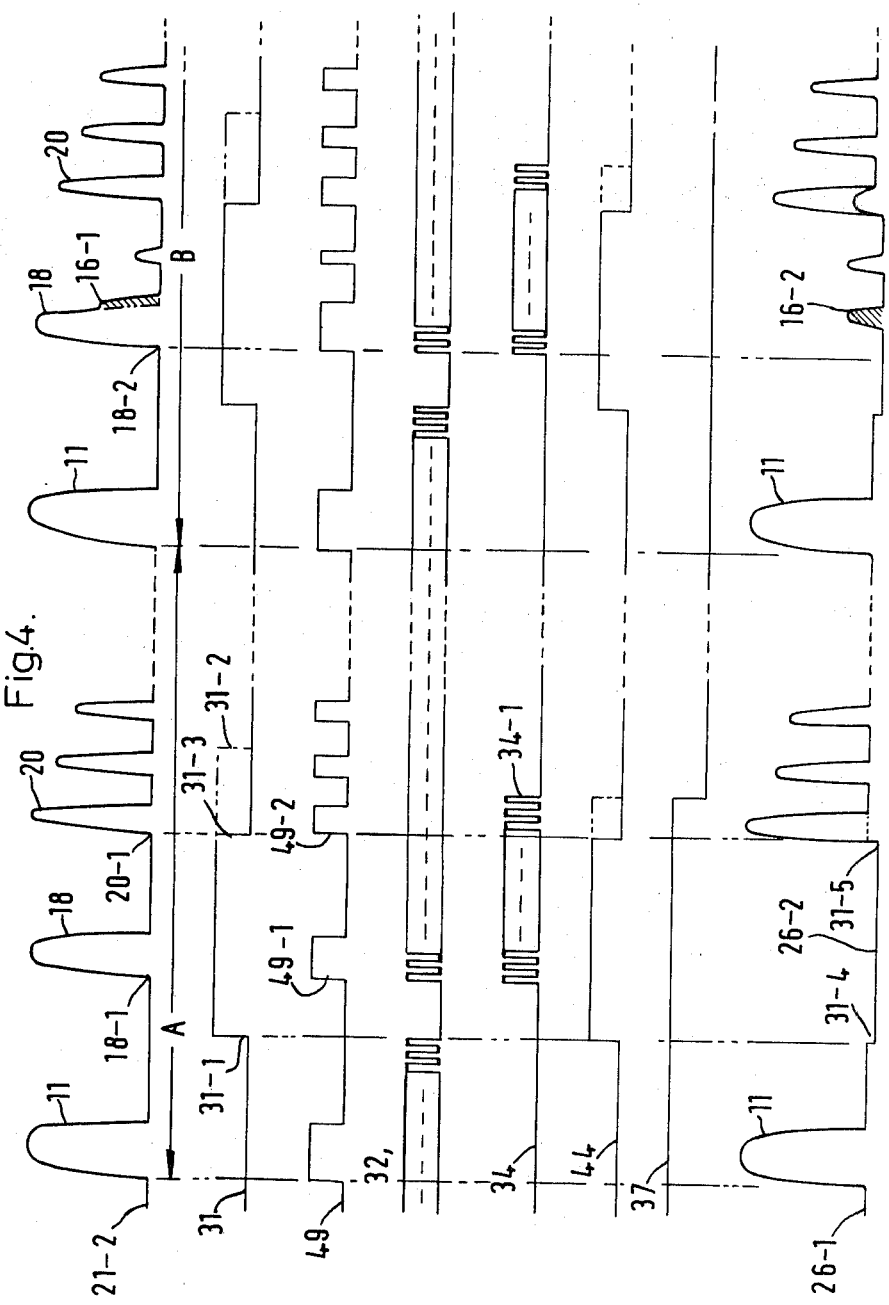

APPARATUS FOR ULTRASONIC EXAMINATION

This invention relates to apparatus for ultrasonic examination wherein an object to be examined is exposed to impulses, i.e. bursts, of ultrasound. Each impulse is reflected by the object as a succession of echoes comprising primarily an echo from the front surface of the object, an echo from any flow, i.e. any discontinuity, that may be present in the object between its front and rear surfaces, and finally an echo from the year surface itself. The purpose of the examination is to detect the flaw. It may occur however that the flaw lies so close to the front surface that the flaw echo occurs within the duration of the front surface echo. In such a case the usually relatively small flaw echo is virtually indistinguishable from front surface echo. This is a particular difficulty in engineering components which have to be examined before expensive machining operations are undertaken.

To make possible the examination, the component has to have a machining allowance sufficiently thick for the finished machined envelope of the component to lie clear of the front surface echo of the unmachined blank. This constitutes a waste of sometimes very expensive material. In the case of components which do not require machining, e.g. components made by powder metallurgy, the examination of the surface region is of course impossible in view of the circumstances described.

It is an object of this invention to provide apparatus for ultrasonic examination which makes it possible to distinguish between a front surface echo and a flaw echo lying within the duration of the front surface echo.

According to this invention there is provided apparatus for ultrasonic examination comprising:

a unit for emitting electrical impulses of ultrasonic frequency at given intervals of time and for receiving from each said impulse a succession of impulses being echoes of said emitted impulse, an analogue to digital converter for converting at least a selected part of each said succession into a series of binary numbers, a memory connected to said converter for storing the series pertaining to a first said succession, and a subtracter having a first input connected to said memory to receive said stored series therefrom and having a second input connected to receive from said converter the series pertaining to a second said succession, the subtracter having an output being the difference between said first and second series.

In use the unit is connected to a transducer for converting the emitted electrical impulses into ultrasonic impulses directed at the object, and the transducer is moved across the front surface of the object to be examined. Then, inasmuch as the first succession of echoes does not contain a flaw echo while the second succession is different from the first succession due to the presence of the flaw echo, the subtracter provides a comparison between the two successions and therefore a discrete indication of the flaw.

An example of apparatus according to this invention will now be described with reference to the accompanying drawings wherein:

FIG. 4 is a timing diagram.

THE APPARATUS

Figure 1:
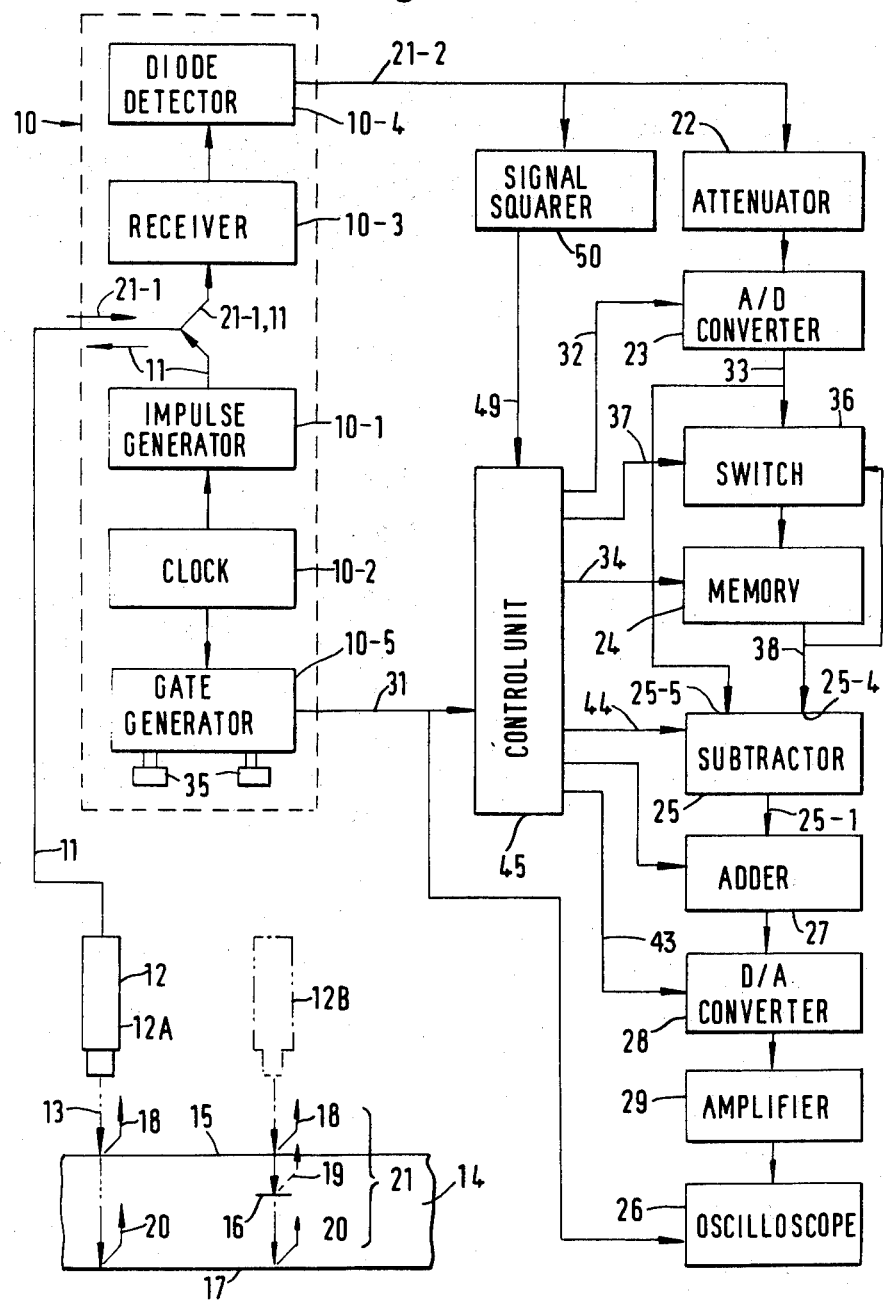
FIG. 1 is a diagram of the apparatus.

Referring to FIG. 1 an emitter/receiver unit 10 has an emitter 10-1 for electrical impulses 11 of ultrasonic frequency. The impulses are repeated at regular intervals of time determined by a clock 10-2 and pass to a transducer 12 connected to the unit 10. The transducer converts the impulses 11 into ultrasonic impulses 13 directed toward a work piece 14. The transducer is moved mechanically in a direction parallel to the front surface 15 of the work piece, i.e. the surface confronting the transducer. During its movement the transducer passes through a first position 12A at which the work piece is assumed to be free from flaws and a second position 12B at which the work piece is assumed to have a flaw 16. Each impulse 13 produces in the work piece a succession of echoes referred to as the signal 21. In the position 12A of the transducer the signal 21 includes an echo 18 from the front surface 15 and a later echo 20 from the rear surface, denoted 17, of the work piece. In position 12B the signal 21 has additionally an echo 19 from the flaw 16. Successive signals 21 are received by the transducer which converts them into electrical signals 21-1 received by a receiver 10-3. The receiver output is passed through a diode detector 10-4 whose output is formed by signals 21-2 in which the echoes 18,19 or 20 appear as envelopes of the positive values of the signals 21-2 (FIG. 4) in accordance with the action of the diode detector. Since the receiver inevitably apprehends the signal 11, the later signal also appears in the signal 21-2. As described so far the apparatus is known.

THE COMPARISON PROCESS

In accordance with the invention the signals 21-2 (FIG. 1) are fed through an attenuator 22 to an analogue-to-digital converter 23 whose output 33 is connected to a memory 24 having an output 38 connected to one input terminal 25-4 of a subtracter 25. The output 33 is also connected directly to the other input terminal 25-5 of the subtracter. As will be described in detail, the memory 24 is switched to store every nth signal 21-2 and the subtracter operates to form the difference between the stored and unstored signals 21-2 i.e. between the outputs 33,38. In other words the subtracter provides a comparison between the outputs 33,38. If the latter outputs are the same, the output denoted 25-1 of the subtracter is zero. On the other hand, if the stored signal 21-2 was derived from the position 12A of the transducer 12 (no flaw) while the unstored signal 21-2 was derived from the position 12B of the transducer, or vice versa, then the outputs 33,38 differ to the extent of the flaw echo 19 and the subtracter output 25-1 will be a discrete indication of the flaw 16.

The output 25-1 (FIG. 1) is passed is succession through an adder 27 (used for setting the base level of this output), a digital-to-analogue converter 28 and an amplifier 29. The output of the amplifier is displayed by an oscilloscope 26 whose output is shown as a signal 26-1 in FIG. 4.

FIG. 4 shows two complete cycles A,B each as determined by the clock 10-2 (FIG. 1). The cycle A is as generated at the position 12A of the transducer 12 (no flaw) while the cycle B corresponds to the position 12B of the transducer where there is a flaw 16 in the work piece. The flaw appears at 16-1 in cycle B. The comparison provided by the subtracter 25 is effectively a comparison between the cycles A,B and the outcome of the comparison is shown as the excursion 16-2 at the oscilloscope display signal 26-1 (FIG. 4). If there is no flaw the signal 26-1 remains at a straght time base line as at 26-2. The signal 21 is repeated with sufficient frequency say 400 to 1000 Hz to provide a visually continuous oscilloscope display. The memory 24 is updated sufficiently frequently in relation to the speed at which the transducer is moved to ensure that a flaw is not passed over without detection. For the purpose of such updating no notice is taken of whether the signal comes from a good part or from a flawed part of the work piece. Further, only a certain part of the signal 21-2 is needed for the purpose of comparison this being the part lying between the beginning of the front surface echo 18 and the beginning of the rear surface echo 20. Although the invention is concerned with the detection of flaws close to the front surface, i.e. flaws likely to be obscured by the front surface echo, it is convenient to include the whole depth of the work piece between the front and rear surfaces in the same comparison process as the immediate front surface region. However, any secondary echoes being part of the signal 21-2 occurring after the beginning of the rear surface echo can be, and are, excluded from the comparison routine as being irrelevant. Likewise the signal 11 which, as mentioned, cannot be excluded from being read by the receiver 10-3, is excluded.

THE CONTROL SEQUENCE

During initial setting up of the apparatus and for the purpose of selecting the relevant part of the signal 21-2 for comparison a manual switch 30 (FIG. 3), is set to render the subtracter 25 inoperative so that, effectively, the memory 24 is bypassed and the subtracter output 25-1 is equal to the output 33. The full signal 21-2 is then displayed as the signal 26-1 of the oscilloscope. Next, a gate signal 31 is set to restrict the duration over which the comparison process is operated.

The signal 31 generated by the clock 10-2 is settable mannually by control knobs 35 at the unit 10. The signal 31 has a rising and a falling edge 31-1,31-3 (FIG. 4) which shows up as vertical offsets 31-4,31-5 in the visual signal 26-1 shown by the oscilloscope. The operator controls the knobs 35 in the sense of moving the edges 31-4,31-5 until the edge 31-4 lies between the impulse 11 and the echo 18, and the edge 31-5 coincides with the beginning of the echo 20. Thereafter the switch 30 is set to render the subtracter operative again thereby restoring the comparison process. In this way irrelevant parts of the signal 21-2, e.g. the impulse 11 and said secondary echoes, are excluded from the comparison process. The gate signal 31 is also used for timing the comparison process, i.e. it determines the beginning and end of a control sequence for carrying out the comparison process.

Figure 2:
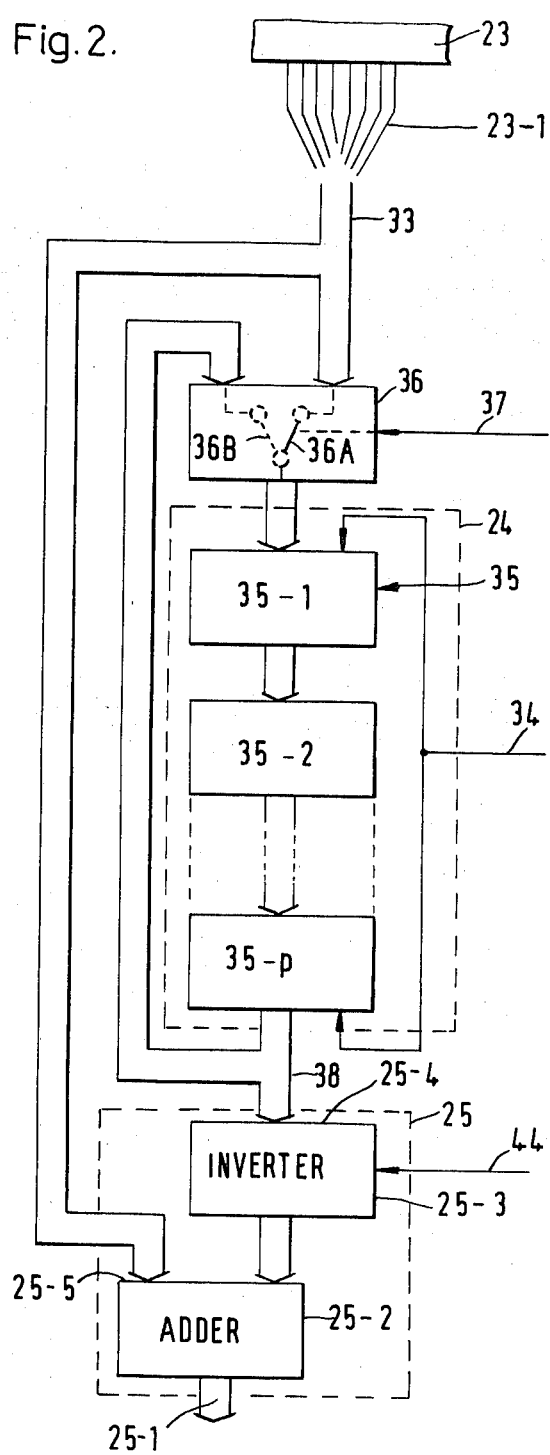
FIG. 2 is an enlarged detail of FIG. 1 showing a memory and subtracter contained in the apparatus.
Figure 3:
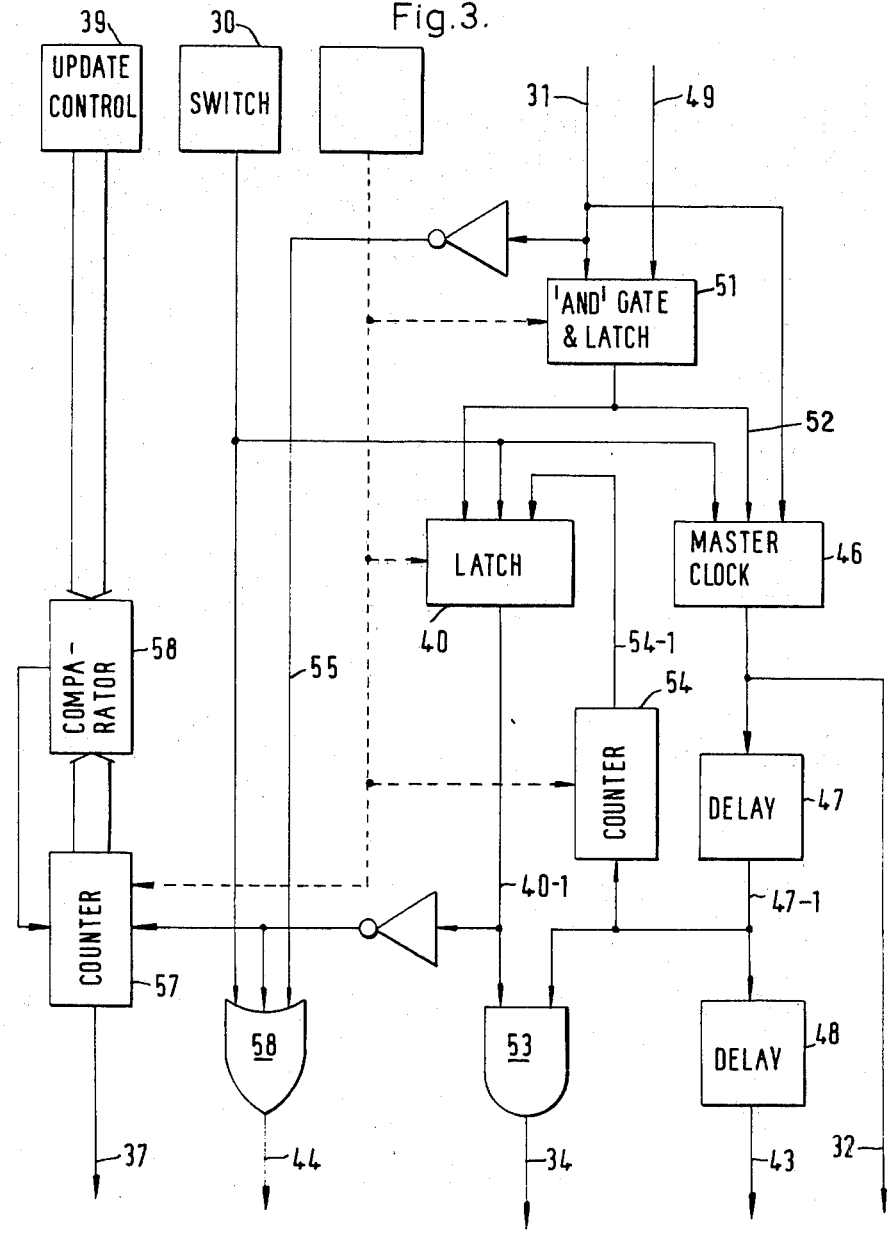
FIG. 3 is an enlarged detail of FIG. 1 showing a control unit contained in the apparatus.

Referring now to the operation of the memory 24, the converter 23 (FIG. 1) is operated by a timing signal 32 which is a pulse signal generated by a master clock 46 (FIG. 3). Each pulse of the signal 32 activates the converter 23 to convert the instantaneous voltage of the analogue signal 21-2 into a binary signal whose digits are output simultaneously on respective parallel lines 23-1 (FIG. 2). The output signal 33 of the converter 23 therefore comprises a series of binary signals presented in succession in accordance with the timing of the pulses of the with pulses of the signal 32. The operation of such converters is well known per se. While, as described, the signal 33 passes directly to the subtracter 25, the entry of the signal 33 to the memory 24 is controlled by a switch 36 (FIG. 2) settable between a position 36A in which the signal 33 is connected to the input of the memory 24 and a position 36B in which the latter input is connected to the output 38 of the memory for the purpose of recirculating the stored signal. The switch 36 is operated by a control signal 37 whereby the memory can be updated with a new signal 33 at any required time.

The memory 24 (FIG. 2) itself comprises a number of serially connected memory units 35 (35-1 to 35-p) each capable of storing one of the binary numbers of the signal 33. The units 35 are of the FIFO type. The expression "FIFO" means "first in, first out" and relates to the property of the memory that as successive binary numbers of the signal 33 are presented at the first unit 35-1 they are shifted, by successive timing signals 34, from unit to unit until all the binary numbers of the signal 33 are contained in the respective units. The first number to have been entered at the first unit 35-1 is then the first number ready to be output at the unit 35-p. Such memories are known per se. The signal 34 is synchronised with the signal 32. When a signal 33 is to be entered into the memory 24, the switch 36 is held in the position 36A sufficiently long for the whole of the signal 33 to be entered into the memory. During such entry the numbers of the previous signal 33 are progressively read out of the memory and this is then the last time at which the old number reaches the subtracter. Before the next series of the signal 33 commences the switch 36 is returned to the position 36B.

The subtracter 25 (FIG. 2) is operated by a timing signal 44 to read each number of the signal 33 simultaneously with the number of the signal 38 present at the memory unit 35-p. In this way the subtracter forms the difference 25-1 of the signals 33,38 progressively number by number. Such subtracters are known per se. In the present example the subtracter comprises an adder 25-2 and an inverter 25-3 and the signal 44 is arranged to switch the inverter on and off. For the purpose of the initial setting up described hereinabove, the manual switch 30 (FIG. 3) is set to hold the inverter off so that the input to the adder is zero and the subtracter output 25-1 is equal to the signal 33.

The D/A converter 28 (FIG. 1) operates in reverse order to the converter 23 and is pulsed by a timing signal 43 synchronized with the signals 32,34 by being derived from the signal 32 through delays 47, 48.

The signals 32,34,37,43 and 44 are produced by a control unit 45 (FIG. 3) performing a control sequence following the rising edge 31-1 (FIG. 4) of the signal 31 when the latter comes on in accordance with the manual setting of the knobs 35 previously described. The actual start of the control sequence arises as follows. A signal square 50 is arranged to respond to any rise above a given threshold from zero of the signal 21-2 to produce a signal 49 (FIG. 4). The signal 49 has a rising edge 49-1 corresponding to the start 18-1 of the echo 18, and is the starting signal for said control sequence. The start of the control sequence by the beginning of the echo ensures a correct timed relationship between the signals 33,38. The signals 31,49 are fed to an AND gate and latch unit 51 where the edge 49-1 produces a signal 52 connected to start the master clock 46. The clock 46 was previously stopped by the edge 31-1 to ensure that this clock can start afresh for every beginning of the echo 18.

The timing signal 32 for the converter 23 is derived directly from the output of the clock 46. The timing signal 34 for the memory 24 is derived from the signal 32 as taken through the delay 47 and an AND gate 53. The latter gate is controlled by a counter 54 set to provide a pulse output 54-1 at the end of a predetermined number of pulses 47-1 output by the delay 47. The output 54-1 is taken to a latch 40 having a continuous output 40-1 to the AND gate 53. The number of pulses 47-1 necessary to produce one pulse 54-1 is that required to completely fill or recirculate the memory 24. To provide a safety margin the capacity of the memory is greater than the greatest distance between the front and rear surface 15,17 for which the apparatus is specified, but, as will be seen, the actual comparison process is terminated at the beginning 20-1 of the rear surface echo 20.

The control signal 37 for updating the memory is produced by a counter 57 driven through an inverter to the output 40-1 by count the number of times the output 40-1 is off. The counter 57 is connected to a comparator 58 preset by a manual update control 39 to a given number being the number of times the comparison process is to be carried out before the memory 24 is updated. When the counter 57 reaches the number preset in the comparator, the latter resets the counter 57 to zero, and this reset is arranged to produce the signal 37 in the sense setting the switch 36 (FIG. 2) to the position 36A. The switch 36 reverts to the position 36B when the counter 57 departs from zero when the next signal 40-1 goes off.

The timing signal 44 for the subtracter 25 is taken from the inverted signal 40-1 acting through an OR gate 58. The arrangement is such that the inverter 25-3 of the subtracter is enabled when the signal 34 is on. The inverter 25-3 would ordinarily be disabled and held at zero when the signal 34 is off. However, as mentioned, the signal 44 is arranged to go off at the beginning 20-1 of the echo 20. This is done in response to the falling edge 31-3 of the signal 31 which had been adjusted during initial setting up and by visual sighting of the display 26-1, to go off when the echo 20 starts. The signal 31 acts on the signal 44 through a connection 55 into its OR gate 58.

With the occurrence of the falling edge 31-3 the comparison process ends. For convenience the master clock 46 is left to go on so that the signal 33 continues to go straight through the subtracter 25 and converter 28 and is displayed on the oscilloscope. The master clock 46 is of course switched off at the beginning of the control sequence of the cycle B. The cycle A itself ends with the beginning of the pulse 11 of the cycle B.

The gate signal 31 is derived from a gate signal generator 10-5 forming a known part of the unit 10 (FIG. 1).

The analogue-to-digital converter 23 may be arranged between the receiver and the diode detector instead of between the diode detector and the memory.

In the example described the comparison process is terminated with the falling edge 31-3 of the gate signal 31 which, as shown in FIG. 4, occurs ahead of the edge 34-1 which denotes the end of the activation of the memory 24 by the signal 40-1 (FIG. 3). However, the signal 31 may be set to occur at 31-2 after the edge 34-1. In that case the activation of the memory is stopped by the counter signal 54-1.

I claim:

1. Apparatus for ultrasonic examination of an object comprising:

a unit for emitting analogue electrical impulses of ultrasonic frequency at given intervals of time and for receiving in respect of each emitted impulse an impulse being an echo of said emitted impulse, said unit being movable with respect to a surface of said object whereby each emitted impulse is incident to a different portion of said surface, an analogue to digital converter for converting each of said echo impulses into a digital number, a memory connected to said converter for storing the digital number pertaining to a first echo impulse.

a subtractor having a first input connected to said memory to receive said stored digital number therefrom and having a second input connected to receive from said converter the digital number pertaining to a second echo impulse, the subtractor having an output being the difference between said digital numbers, and switch means arranged between the converter and the memory and being settable to one of two conditions, wherein in the one condition the input end of the memory is connected to the output end of the memory thereby to cause the memory to recirculate, and in the other one of said conditions the input end of the memory is connected to said converter to receive output signals therefrom.

2. Apparatus according to claim 1 comprising means for producing a signal during each said interval, means responsive to a count of successive said signals for setting said switch to the other one of said conditions once for a predetermined plurality of said signals.

3. Apparatus according to claim 1, comprising means for producing, during each said interval, a timing signal set to render said memory inoperative prior to the occurance of a selected one of the echo impulses, and means responsive to the start of said selected impulse for rendering the memory operative again.

4. Method of ultrasonic examination of an object for internal faults, using apparatus comprising means for generating at successive intervals of time electrical impulses of ultrasonic frequency, a transducer for converting said impulses into ultrasonic impulses and for converting echoes of the latter impulses into corresponding electrical signals, said transducer being movable across a surface of said object, a surface and fault echo being receivable substantially simultaneously from said surface and from a fault in said object close to said surface, wherein the method comprises imparting movement to said transducer across said surface, and during said movement of the transducer automatically and electronically performing the operations of reading a first signal produced from an echo, storing said first signal, reading a second signal arising from an echo received at an interval of time later than the interval at which said first signal arose, the signals therefore pertaining to respective first and second locations of said transducer during said movement thereof, and forming a third signal which is the difference between said first and second signals and therefore being a signal from which said surface echo has been eliminated, said third signal being a discrete indication of a fault close to said surface when such a fault is present at one of said locations.

5. Method according to claim 4, comprising electronically and automatically performing and repeating a cycle comprising storing a said first signal for a predetermined period of time, comparing successive second signals occurring during said period with said stored signal, and at the end of said period reading and storing a new first signal.

* * * * *